(12) United States Patent
Crinean (10) Patent No.: US 8,795,689 B2
(45) Date of Patent: *Aug. 5, 2014

(54) **METHOD FOR CONTROLLING *STREPTOCOCCUS PNEUMONIAE* SEROTYPE 19A POLYSACCHARIDE MOLECULAR WEIGHT**

(75) Inventor: Jean Heather Crinean, Sanford, NC (US)

(73) Assignee: Wyeth LLC, New York, NY (US)

( * ) Notice: Subject to any disclaimer, the term of this patent is extended or adjusted under 35 U.S.C. 154(b) by 37 days.

This patent is subject to a terminal disclaimer.

(21) Appl. No.: 12/640,769

(22) Filed: Dec. 17, 2009

(65) Prior Publication Data
US 2010/0158953 A1  Jun. 24, 2010

Related U.S. Application Data

(60) Provisional application No. 61/138,563, filed on Dec. 18, 2008.

(51) Int. Cl.
*A61K 39/09* (2006.01)
(52) U.S. Cl.
USPC ...................................................... 424/244.1
(58) Field of Classification Search
None
See application file for complete search history.

(56) References Cited

U.S. PATENT DOCUMENTS

| | | | |
|---|---|---|---|
| 4,221,906 A | 9/1980 | Querry et al. | |
| 4,686,102 A | 8/1987 | Ritchey et al. | |
| 5,623,057 A | 4/1997 | Marburg et al. | |
| 5,714,354 A | 2/1998 | Arnold et al. | |
| 5,847,112 A | 12/1998 | Kniskern | |
| 6,146,902 A | 11/2000 | McMaster | |
| 6,743,610 B2 | 6/2004 | Donnelly et al. | |
| 7,709,001 B2 | 5/2010 | Hausdorff et al. | |
| 7,718,791 B2 | 5/2010 | Bahler et al. | |
| 2006/0228380 A1 | 10/2006 | Hausdorff et al. | |
| 2006/0228381 A1 | 10/2006 | Bahler et al. | |
| 2007/0065460 A1 | 3/2007 | Hamidi et al. | |
| 2007/0184071 A1 | 8/2007 | Hausdorff et al. | |
| 2007/0184072 A1 | 8/2007 | Hausdorff et al. | |
| 2007/0231340 A1 | 10/2007 | Hausdorff et al. | |
| 2008/0102498 A1 | 5/2008 | Bahler et al. | |
| 2008/0286838 A1* | 11/2008 | Yuan et al. | 435/101 |
| 2010/0160622 A1 | 6/2010 | Crinean | |

FOREIGN PATENT DOCUMENTS

| | | |
|---|---|---|
| EP | 0002404 | 11/1978 |
| EP | 0024493 | 6/1980 |
| EP | 0072513 | 8/1982 |
| EP | 0497524 | 1/1992 |
| EP | 1762245 | 12/1999 |
| WO | WO8201995 | 6/1982 |
| WO | WO0168903 | 9/2001 |
| WO | WO2006110352 | 10/2006 |
| WO | WO2007052168 | 5/2007 |
| WO | WO2008118752 | 10/2008 |

OTHER PUBLICATIONS

Massaldi et al., "Features of bacterial growth and polysaccharide production of *Streptococcus pneumoniae* serotype 14," Biotechnology and Applied Biochemistry, 55(1):37-43 (2010).
Scott (1968). Periodate oxidation, $pK_a$ and conformation of hexuronic acids in polyuronides and mucopolysaccharides. *Biochem. Biophys. Acta*, 170:471-473.
Larsen and Painter (1969). The periodate-oxidation limit of alginate. *Carbohyd. Res.*, 10:186-187.
Crater, D. L., et al., "Hyaluronic Acid Synthesis Operon (has) Expression in Group A Streptococci", The Journal of Biological Chemistry, 1995, 18452-18458, vol. 270, No. 31.
Hathaway, L J., et al., "In vitro expression of the first capsule gene of *Streptococcus pneumoniae*, cpsA, is associated with serotype-specific colonization prevalence and invasiveness", Microbiology, 2007, 2465-2471, vol. 153.
McDougal, L. K., et al., "Analysis of multiply antimicrobial-resistant isolates of *Streptococcus pneumoniae* from the United States", Antimicrobial Agents and Chemotherapy, 1992, 2176-2184, vol. 36, No. 10.
Paoletti, L. C., et al., "Cell growth rate regulates expression of group B *Streptococcus* type III capsular polysaccharide", Infection and Immunity, 1996, 1220-1226, vol. 64, No. 4.
Fernebro, J., et al., "Capsular Expression in *Streptococcus pneumoniae* Negatively Affects Spontaneous and Antibiotic-Induced Lysis and Contributes to Antibiotic Tolerance", Capsular Expression and Lysis in *S. pneumoniae*, 2004, 328-338, vol. 89.
Regev-Yochay, G., et. al., "SpxB Is a Suicide Gene of *Streptococcus pneumoniae* and Confers a Selective Advantage in an In Vivo Competitive Colonization Model", Journal of Bacteriology, 2007, 6532-6539, vol. 189(18).

(Continued)

*Primary Examiner* — Gary B. Nickol
*Assistant Examiner* — Khatol Shahnan-Shah
(74) *Attorney, Agent, or Firm* — Mathew J. Pugmire (57) ABSTRACT

The present invention provides improved methods for producing a solution containing high molecular weight isolated *Streptococcus pneumoniae* 19A capsular polysaccharides. In certain methods, a fermentation culture of *Streptococcus pneumoniae* bacterial cells that produce serotype 19A capsular polysaccharides is fermented for less than 6 hours before the bacterial cells are lysed the capsular polysaccharides are harvested. In other methods, $CO_2$ is supplied to the fermentation culture. Supplying $CO_2$ to the fermentation culture includes adding bicarbonate ions to the fermentation culture, adding carbonate ions to the fermentation culture, adding mixtures of bicarbonate and carbonate ions to the fermentation culture, and overlaying the fermentation culture with $CO_2$.

16 Claims, 6 Drawing Sheets

(56) References Cited

OTHER PUBLICATIONS

Wartha, F., et al., "Capsule and D-alanylated Lipoteichoic Acids Protect *Streptococcus pneumoniae* Against Neutrophil Extracellular Traps", Cellular Microbiology, 2007, 1162-1171, vol. 9(5).

Henrichsen, et al., "Production of monovalent antisera by induction of immunological tolerance for capsular typing of *Streptococcus pneumoniae*," FEMS Microbiol Lett, 1992, vol. 94, pp. 89-94.

Katzenellenbogen, et al., "Structural Determination of the Capsular Polysaccharide of *Streptococcus pneumoniae* TYPE* 19A (57)**," Carbohydrate Res., 1983, vol. 124, pp. 235-245.

Klugman, et al., "A Trial of a 9-Valent Pneumococcal Conjugate Vaccine in Children with and Those without HIV Infection," New England Journal of Medicine, 2003, vol. 349(14), pp. 1341-1348.

Lagos, et al., "Immunology of combining CRM197 conjugates for *Streptococcus pneumoniae, Neisseria meningitis* and *Haemophilus influenzae* in Chilean infants," Vaccine, 2009, vol. 17(17), pp. 2299-2305.

Lazar, et al., Transforming growth factor alpha: mutation of aspartic acid 47 and leucine 48 results in different biological activities, Molecular Cell Biol, 1988, vol. 8(3), pp. 1247-1252.

Mallet, E., et al., "Immunogenicily and safety of a CRM197 conjugated 9-valent pneumococcal and meningococcal C combination vaccine in healthy infants," Poster for the 25th Annual Meeting of the European Society for Paediatric Infectious Diseases (ESPID), Porto, Portugal, May 2-4, 2007.

O'Brien, et al., "Efficacy and safety of seven-valent conjugate pneumococcal vaccine in American Indian children: group randomised trial," Lancet, 2003, vol. 362, pp. 355-361.

Saeland, et al., "Serum Samples from Infants Vaccinated with a Pneumococcal Conjugate Vaccine, PncT, Protect Mice against Invasive Infection Caused by *Streptococcus pneumoniae* Serotypes 6A and 6B," Journal of Infectious Diseases, 2001, vol. 183(2), pp. 253-260.

Constantino, et al, "Size fractionation of bacterial capsular polysaccharides for theiruse in conjugate vaccines," Vaccine, 1999, vol. 17(9-10), pp. 1251-1263.

Goncalves, et al, "Optimization of medium and cultivation conditions for capsular polysaccharide production by *Streptococcus pneumoniae* serotype 23F," Applied Microbiology & Biotechnology, 2002, vol. 59(6) pp. 713-717.

Goncalves, et al., "Purification of capsular polysaccharide from *Streptococcus pneumoniae* scrotype 23F by a procedure suitable for scale-up," Biotechnology & Applied Biochemistry, 2003, 37 (Pt.3), pp. 283-287.

Pujar, et al., "Base Hydrolysis of Phosphodiester Bonds in Pneumococcal Polysaccharides," Biopolymers, 2004, 75:71-84.

\* cited by examiner

METHOD FOR CONTROLLING *STREPTOCOCCUS PNEUMONIAE* SEROTYPE 19A POLYSACCHARIDE MOLECULAR WEIGHT

This application claims benefit of priority to U.S. Provisional Application No. 61/138,563, which was filed on 18 Dec. 2008, and which is incorporated herein by reference in its entirety.

FIELD OF THE INVENTION

The invention relates to methods for increasing the molecular weight of isolated *Streptococcus pneumoniae* serotype 19A capsular polysaccharides by controlling harvest time.

BACKGROUND

In the preparation of multivalent conjugate pneumococcal vaccines directed to the prevention of invasive diseases caused by the organism *Streptococcus pneumoniae* (also known as pneumococcus), selected *Streptococcus pneumoniae* serotypes are grown to supply polysaccharides needed to produce the vaccine. The cells are grown in fermentors with lysis induced at the end of the fermentation by addition of sodium deoxycholate or an alternate lysing agent. The lysate broth is then harvested for downstream purification and the recovery of the capsular polysaccharide which surrounds the bacterial cells. After conjugation with a carrier protein, the polysaccharide is included in the final vaccine product and confers immunity in the vaccine's target population to the selected *Streptococcus pneumoniae* serotypes.

Polysaccharide size is a quality attribute that is assayed in each preparation batch and must be appropriately controlled. With respect to *Streptococcus pneumoniae* serotype 19A polysaccharides, the size of the polysaccharide can be affected by parameters such as fermentation pH, fermentation temperature, and hold temperatures. Furthermore, thermal degradation of 19A polysaccharides occurs across both fermentation/recovery and purification processes, which provides an additional challenge for successfully addressing and controlling various parameters when scaling-up production processes for the large-scale manufacture of 19A polysaccharides.

Accordingly, improved methods for the recovery of high molecular weight serotype 19A capsular polysaccharides from cellular *Streptococcus pneumoniae* lysates are needed.

BRIEF SUMMARY OF THE INVENTION

Improved methods for the recovery of high molecular weight serotype 19A capsular polysaccharides from cellular *Streptococcus pneumoniae* lysates are provided. In one method, a fermentation culture of *Streptococcus pneumoniae* bacterial cells that produce serotype 19A capsular polysaccharides is fermented for less than 6 hours before the bacterial cells are lysed and the capsular polysaccharides are harvested. Accordingly, in one embodiment of the invention, the method includes the steps of: 1) preparing a fermentation culture of *Streptococcus pneumoniae* bacterial cells that produce serotype 19A capsular polysaccharides; 2) fermenting the fermentation culture for less than 6 hours; 3) lysing the bacterial cells in the fermentation culture; and 4) isolating *Streptococcus pneumoniae* serotype 19A capsular polysaccharides from the fermentation culture; whereby a solution containing high molecular weight isolated *Streptococcus pneumoniae* serotype 19A capsular polysaccharides is produced. In a particular embodiment, the fermentation culture is fermented for less than 5 hours. In a further embodiment, the fermentation culture is fermented for less than 4 hours. In another embodiment, the fermentation culture is fermented for between 3 hours and 6 hours. In another embodiment, the molecular weight of the isolated *Streptococcus pneumoniae* capsular polysaccharide is at least 480 kDa.

In another embodiment of the present invention, the method also involves supplying $CO_2$ to a fermentation culture of bacterial cells that produce *Streptococcus pneumoniae* serotype 19A polysaccharides. Accordingly, in one embodiment the method of the present invention includes the steps of: 1) preparing a fermentation culture of *Streptococcus pneumoniae* bacterial cells that produce serotype 19A capsular polysaccharides; 2) supplying $CO_2$ to the fermentation culture; 3) fermenting the fermentation culture for less than 6 hours; 4) lysing the bacterial cells in the fermentation culture; and 5) isolating *Streptococcus pneumoniae* serotype 19A capsular polysaccharides from the fermentation culture; whereby a solution containing high molecular weight isolated *Streptococcus pneumoniae* serotype 19A capsular polysaccharides is produced. In a particular embodiment, supplying $CO_2$ to the fermentation culture includes adding bicarbonate ion ($HCO_3^-$) to the fermentation culture, for example, adding $NaHCO_3$ (sodium bicarbonate) to the fermentation culture. In a further embodiment, supplying $CO_2$ to the fermentation culture includes adding carbonate ion ($CO_3^{2-}$) to the fermentation culture, for example, adding $Na_2CO_3$ (sodium carbonate) to the fermentation culture. In another embodiment, supplying $CO_2$ to the fermentation culture includes a first addition of $NaHCO_3$ and a second addition of $Na_2CO_3$. In yet another embodiment, supplying $CO_2$ to the fermentation culture includes overlaying the fermentation culture with $CO_2$. In another embodiment, the molecular weight of the isolated *Streptococcus pneumoniae* capsular polysaccharide is at least 480 kDa.

In another embodiment, the present invention relates to a solution containing high molecular weight *Streptococcus pneumoniae* serotype 19A capsular polysaccharides, where the solution is produced by any of the methods described above.

DETAILED DESCRIPTION OF THE INVENTION

*Streptococcus pneumoniae* are Gram-positive, lancet shaped cocci that are usually seen in pairs (diplococci), but also in short chains or as single cells. They grow readily on blood agar plates with glistening colonies and display alpha hemolysis unless grown anaerobically where they show beta hemolysis. The cells of most pneumococcal serotypes have a capsule which is a polysaccharide coating surrounding each cell. This capsule is a determinant of virulence in humans, as it interferes with phagocytosis by preventing antibodies from attaching to the bacterial cells. Currently there are more than 90 known pneumococcal capsular serotypes identified, with the 23 most common serotypes accounting for approximately 90% of invasive disease worldwide.

As a vaccine, the pneumococcal polysaccharide coat can confer a reasonable degree of immunity to *Streptococcus pneumoniae* in individuals with developed or unimpaired immune systems, but a conjugated protein with polysaccharide allows for an immune response in infants and elderly who are also most at risk for pneumococcal infections. The pneumococcal cells are grown in fermentors with lysis induced at the end of the fermentation. The lysate broth is then harvested for downstream purification and the recovery of the capsular polysaccharides.

Polysaccharide size is a quality attribute assayed for in each preparation batch and must be appropriately controlled. The molecular weight for serotype 19A capsular polysaccharides is affected by parameters of the fermentation process. The methods of the present invention allow for the recovery of high molecular weight serotype 19A capsular polysaccharides from cellular *Streptococcus pneumoniae* lysates.

In the development of the present methods, the concentration of HySoy and choice of base titrant were modified in an attempt to modify final polysaccharide yields and molecular weights. Four fermentation schemes were tested. The first used a baseline NaOH process with 28 g/L HySoy. The second used 20% sodium carbonate as the base titrant and 20 g/L HySoy. The third combined advantages of the first two approaches by introducing carbonate through the batching of sodium bicarbonate and using a mixed NaOH/carbonate base titrant. The fourth approach used carbonate as the base titrant with a 10 mM bicarbonate addition to bolster growth.

Using NaOH as the base titrant during fermentation had the advantage of being able to lower the deoxycholate lysate to pH 5.0 without foaming to remove protein and improve filtration, but resulted in lower molecular weight polysaccharide (<450 kDa). $Na_2CO_3$ provided higher molecular weight but had foaming issues if the pH of the deoxycholate lysate was lowered. At a higher pH hold step of 6.6, the fermentations using $Na_2CO_3$ formed a gel-like material, with subsequent filtration problems. Minimizing the amount of $Na_2CO_3$ by using a blend of NaOH and $Na_2CO_3$ as a pH titrant provided the molecular weight size benefits of $Na_2CO_3$ while eliminating foaming and filtration problems due to the sudden release of large amounts of $CO_2$. The use of 20% $Na_2CO_3$ (w/v) as the base titrant with a 10 mM $NaHCO_3$ addition to bolster growth (fourth approach) produced consistent, high molecular weight polysaccharides at high yield.

In addition to HySoy concentration and base titrant, the effect of harvest time on *Streptococcus pneumoniae* serotype 19A capsular polysaccharide molecular weight was also studied. It was found that allowing the fermentation culture to ferment for less than 6 hours before lysis of the bacterial cells produced high molecular weight serotype 19A capsular polysaccharides from cellular *Streptococcus pneumoniae* lysates.

The present invention thus provides improved methods for the recovery of high molecular weight serotype 19A capsular polysaccharides from cellular *Streptococcus pneumoniae* lysates. In one method, a method for producing a solution containing high molecular weight isolated *Streptococcus pneumoniae* serotype 19A capsular polysaccharides is provided, which includes the steps of: 1) preparing a fermentation culture of *Streptococcus pneumoniae* bacterial cells that produce serotype 19A capsular polysaccharides; 2) fermenting the fermentation culture for less than 6 hours; 3) lysing the bacterial cells in the fermentation culture; and 4) isolating *Streptococcus pneumoniae* serotype 19A capsular polysaccharides from the fermentation culture; whereby a solution containing high molecular weight isolated *Streptococcus pneumoniae* serotype 19A capsular polysaccharides is produced. In certain embodiments, the fermentation culture is fermented for less than about 7 hours, less than about 6.5 hours, less than about 6 hours, less than about 5.5 hours, less than about 5 hours, less than about 4.5 hours, less than about 4 hours, or less than about 3.5 hours. In another embodiment, the fermentation culture is fermented for between 3 hours and 7 hours, for between 3 hours and 6.5 hours, for between 3 hours and 6 hours, for between 3 hours and 5.5 hours, for between 3 hours and 5 hours, for between 3 hours and 4.5 hours, for between 3 hours and 4 hours, or for between 3 hours and 3.5 hours. In another embodiment, the present invention relates to a solution containing high molecular weight *Streptococcus pneumoniae* serotype 19A capsular polysaccharides, where the solution is produced by the method described above.

In another embodiment, the method of the present invention also involves supplying $CO_2$ to a fermentation culture of bacterial cells that produce *Streptococcus pneumoniae* serotype 19A polysaccharides, which includes the steps of: 1) preparing a fermentation culture of *Streptococcus pneumoniae* bacterial cells that produce serotype 19A capsular polysaccharides; 2) supplying $CO_2$ to the fermentation culture; 3) fermenting the fermentation culture for less than 6 hours; 4) lysing the bacterial cells in the fermentation culture; and 5) isolating *Streptococcus pneumoniae* serotype 19A capsular polysaccharides from the fermentation culture; whereby a solution containing high molecular weight isolated *Streptococcus pneumoniae* serotype 19A capsular polysaccharides is produced. In another embodiment, the present invention relates to a solution containing high molecular weight *Streptococcus pneumoniae* serotype 19A capsular polysaccharides, where the solution is produced by the method described above.

The methods of the invention produce high molecular weight *Streptococcus pneumoniae* serotype 19A capsular polysaccharides. As used herein, "high molecular weight" refers to molecular weights that are at least about 480 kDa, about 490 kDa, about 500 kDa, about 510 kDa, about 520 kDa, about 525 kDa, about 550 kDa, about 575 kDa, about 600 kDa, about 625 kDa, about 650 kDa, about 675 kDa, about 700 kDa, about 725 kDa, about 750 kDa, about 775 kDa, about 800 kDa, about 825 kDa, about 850 kDa, about 875 kDa, about 900 kDa, about 925 kDa, about 950 kDa, about 975 kDa, or about 1000 kDa.

In certain methods, supplying $CO_2$ to the fermentation culture includes adding bicarbonate ion ($HCO_3^-$) to the fermentation culture, for example, adding $NaHCO_3$ to the fermentation culture. $NaHCO_3$ additions of 5-50 mM can be used, such as 5 mM, 10 mM, 15 mM, 20 mM, 25 mM, 30 mM, 35 mM, 40 mM, 45 mM, or 50 mM. In other methods, supplying $CO_2$ to the fermentation culture includes adding carbonate ion ($CO_3^{2-}$) to the fermentation culture, for example, adding $Na_2CO_3$ to the fermentation culture. $Na_2CO_3$ additions of 0.1 M-2.0 M can be used, such as 0.1 M, 0.2 M, 0.4 M, 0.6 M, 0.7 M, 0.9 M, 1.0 M, 1.5 M, 1.8 M, or 2.0 M. A weight/volume (w/v) equivalent can also be used, such as 5%

(w/v) Na$_2$CO$_3$, 10% (w/v) Na$_2$CO$_3$ or 20% (w/v) Na$_2$CO$_3$. In yet other methods, supplying CO$_2$ to the fermentation culture includes a first addition of NaHCO$_3$ and a second addition of Na$_2$CO$_3$ to the fermentation culture. In further methods, supplying CO$_2$ to the fermentation culture includes overlaying the fermentation culture with CO$_2$. CO$_2$ overlays of 5%-100% can be used, for example, 5%, 10%, 15%, 20%, 25%, 30%, 35%, 40%, 45%, 50%, 55%, 60%, 65%, 70%, 75%, 80%, 85%, 90%, 95%, or 100%.

Within the methods of the present invention, the bacterial cells may be lysed using any lytic agent. A "lytic agent" is any agent that aids in cell wall breakdown and release of autolysin which causes cellular lysis including, for example, detergents. As used herein, the term "detergent" refers to any anionic or cationic detergent capable of inducing lysis of bacterial cells. Representative examples of such detergents for use within the methods of the present invention include deoxycholate sodium (DOC), N-lauryl sarcosine (NLS), chenodeoxycholic acid sodium, and saponins.

In one embodiment of the present invention, the lytic agent used for lysing bacterial cells is DOC. DOC is the sodium salt of the bile acid deoxycholic acid, which is commonly derived from biological sources such as cows or oxen. DOC activates the LytA protein, which is an autolysin that is involved in cell wall growth and division in *Streptococcus pneumoniae*. The LytA protein has choline binding domains in its C-terminal portion, and mutations of the lytA gene are known to produce LytA mutants that are resistant to lysis with DOC.

Although there is no evidence that the use of DOC during *Streptococcus pneumoniae* polysaccharide purification poses a health risk, the use of such biologically derived reagents could raise potential regulatory concerns. Accordingly, in one embodiment of the present invention, the lytic agent used for lysing bacterial cells is a non-animal derived lytic agent. Non-animal derived lytic agents for use within the methods of the present invention include agents from non-animal sources with modes of action similar to that of DOC (i.e., that affect LytA function and result in lysis of *Streptococcus pneumoniae* cells). Such non-animal derived lytic agents include, but are not limited to, analogs of DOC, surfactants, detergents, and structural analogs of choline, and may be determined using procedures as described in the Experimental section herein below. In one embodiment, the non-animal derived lytic agent is selected from the group consisting of decanesulfonic acid, tert-octylphenoxy poly(oxyethylene)ethanols (e.g. Igepal® CA-630, CAS #: 9002-93-1, available from Sigma Aldrich, St. Louis, Mo.), octylphenol ethylene oxide condensates (e.g. Triton® X-100, available from Sigma Aldrich, St. Louis, Mo.), N-lauryl sarcosine sodium (NLS), lauryl iminodipropionate, sodium dodecyl sulfate, chenodeoxycholate, hyodeoxycholate, glycodeoxycholate, taurodeoxycholate, taurochenodeoxycholate, and cholate. In another embodiment, the non-animal derived lytic agent is NLS.

Within the methods of the present invention, *Streptococcus pneumoniae* capsular polysaccharides are isolated using standard techniques known to those skilled in the art. For example, following fermentation of bacterial cells that produce *Streptococcus pneumoniae* serotype 19A capsular polysaccharides, the bacterial cells are lysed to produce a cell lysate. The capsular polysaccharides may then be isolated from the cell lysate using purification techniques known in the art, including the use of centrifugation, precipitation, ultra-filtration, and column chromatography (See, for example, U.S. Patent App. Pub. Nos. 20060228380, 20060228381, 20070184071, 20070184072, 20070231340, and 20080102498).

The process changes described above allow for the recovery of high molecular weight serotype 19A capsular polysaccharides from cellular *Streptococcus pneumoniae* lysates. This is a robust improvement of the fermentation/recovery process that can greatly enhance the production of pneumococcal polysaccharides.

The following examples are offered by way of illustration and not by way of limitation.

EXAMPLES

*Streptococcus pneumoniae* bacterial cells that produce serotype 19A were grown to supply polysaccharides needed to produce vaccines for active immunization against invasive disease caused by *Streptococcus pneumoniae* due to capsular serotypes included in the vaccine. The cells were grown in fermentors with lysis induced at the end of the fermentation. The lysate broth was then harvested for downstream purification and the recovery of the capsular polysaccharides. Because polysaccharide size is a quality attribute assayed for in each preparation batch, polysaccharide size must be appropriately controlled. The molecular weight for serotype 19A capsular polysaccharides was found to be affected by parameters of the fermentation process. The following example describes studies relating to harvest time and the supply of CO$_2$ during fermentation of *Streptococcus pneumoniae* serotype 19A.

Example 1

Carbon Dioxide Supply Effect on Polysaccharide Molecular Weight

Fermentation

Laboratory runs were performed in 3 L Braun Biostat B fermentors (B. Braun Biotech, Allentown, Pa.). They were filled with 1.8 L of HYS medium (20 g/L HySoy, 2.5 g/L NaCl, 0.5 g/L KH$_2$PO$_4$, 0.013 g/L CaCl$_2$.2H$_2$O, 0.15 g/L L-Cysteine HCl). The fermentors were then autoclaved for 60 minutes at 121° C. After cooling, either 40 or 60 mL/L of a 50% Glucose+1% Magnesium Sulfate (w/v) (DMS) solution was added to each unit. If required, sodium bicarbonate was added prior to inoculation.

A 2 L seed bottle containing 1 L of HYS media was inoculated with Type 19A frozen seed stocks and incubated at 36° C. without shaking for approximately 6-8 hours. Inoculation of the fermentors was performed with a volume of 100 mL (~5.2% v/v) aliquoted from a bottle with an OD$_{600}$ between 0.3-0.9 and pH between 4.75-5.60. The fermentation temperature and pH were controlled at the desired setpoints. The standard conditions of 36° C., 1 L/min air overlay, pH controlled to 7 and agitation of 75 rpm were used. Two impellers were placed at the low and middle positions on the agitator shaft. A bottle containing the appropriate base titrant (3 N NaOH, 3 N NaOH blended with various concentrations of NaHCO$_3$, 3 N NaOH blended with various concentrations of Na$_2$CO$_3$ and NaHCO$_3$, and 20% Na$_2$CO$_3$) was hooked up for automatic pH control. The fermentors were sampled at various time points for external pH, OD$_{600}$, glucose, polysaccharide, and protein. The runs were terminated when the glucose concentration was near depletion, or no increase in OD over time was noted.

Optical Density (OD$_{600}$) Measurement

The cellular density of the fermentation broth was determined by reading the absorbance of the samples at 600 nm using a Shimadzu (Columbia, Md.) UV-1601 (2 nm bandwidth) or Spectronics (Westbury, N.Y.) Genesys 5 spectrophotometer (5 nm bandwidth). The unit was blanked with the HYS medium diluted with de-ionized (DI) water to match the dilution required of the sample. The sample was diluted to keep the absorbance below a reading of 0.4, which is well within the linear range of the spectrophotometer.

Glucose Concentration

Glucose levels were determined by centrifuging out the cells and using the supernatant straight or 3× diluted with DI water. The samples were analyzed on a Nova Biomedical (Waltham, Mass.) BioProfile 400.

Polysaccharide Analysis

Samples were taken at the final fermentation reading and treated with 12% sodium deoxycholate (DOC) to a concentration of 0.13% (w/v) and gently agitated. They were held between 8-24 hours at 5° C. then pH adjusted to 5.0 with 50% acetic acid to precipitate out most of the DOC and protein. After another hold interval of 12-24 hours at 5° C., the samples were centrifuged (14000 rpm, Sorvall (Thermo Fisher Scientific, Waltham, Mass.) SS34 rotor, 10 min at 15° C.). The pH of the supernatant was adjusted to 6.0. The supernatant was then filtered through 0.45 μm Pall (East Hills, N.Y.) HT Tuffryn Membrane syringe filters (low protein binding). The filtered product was analyzed by high-performance size exclusion chromatography (HPLC-SEC) using standard methodology well known in the art (see, e.g., Aguilar, M. "HPLC of Peptides and Proteins: Methods and Protocols" Totowa, N.J.: Humana Press (2004)).

Protein Analysis

Protein levels were analyzed by sodium dodecyl sulfate polyacrylamide gel electrophoresis (SDS-PAGE) methods well known in the art (see, e.g., Walker, J. M. "The Protein Protocols Handbook" Totowa, N.J.: Humana Press (2002)). The filtered cell lysate (supernatant) as prepared above was aliquoted into microfuge tubes at 65 μL/tube. Additions of reducing agent (10 μL dithiothreitol (DTT)) and NuPAGE® (Invitrogen, Carlsbad, Calif.) 4× lithium dodecyl sulfate (LDS) sample buffer (25 μL) were made to each sample. The samples were vortexed and heated for 10 minutes prior to 10 μL/lane loading on NuPAGE® 4-12% Bis-Tris 12 well gels. The gels were run in NuPAGE® MES-SDS buffer at 150 V limiting for approximately 60 minutes and subsequently stained using the Zoion staining protocol (Zoion Biotech, Worcester, Mass.). Sample analysis was performed using an UVP Imager (UVP Inc., Upland, Calif.) with LabWorks™ (UVP Inc.) V.3 software to obtain approximate concentrations of specific protein bands of interest. Bovine Serum Albumin (BSA) Fraction V was used to develop a protein standard curve to calculate the approximate protein values of the samples (in lysed cell broth).

Molecular Weight Analysis

Fermentation samples of 1-2 liters were treated with 12% sodium DOC to a concentration of 0.13% (w/v) with agitation at 200 rpm. Samples were held between 8-24 hours at either 5° C. or 20° C. The samples were then pH adjusted to 5.0 or 6.6 with 50% acetic acid to precipitate out most of the DOC and protein. After another hold interval of 12-24 hours at 5° C., the samples were centrifuged (11000 rpm, Sorvall (Thermo Fisher Scientific, Waltham, Mass.) SLA-3000 rotor, 15 min at 10° C.). The supernatant samples were then pH adjusted to 6.0 with 3 N NaOH, and filtered using 0.45 μm Millipore (Billerica, Mass.) MP60 filters. The samples were then subjected to a modified purification process consisting of 100K molecular weight cut-off (MWCO) diafiltration (5× concentration followed by 7.5× diafiltration with DI water), 0.1% HB precipitation, and carbon filtration. The purified material was then subjected to Multi Angle Laser Light Scattering (MALLS) analysis.

Fermentation Process Study

Based on previous studies, the fermentation process was optimized by switching from $Na_2CO_3$ to NaOH as the base titrant. Use of NaOH allowed the recovery pH to be lowered to 5.0 resulting in significant protein precipitation. $Na_2CO_3$ will release $CO_2$ at low pH (<6.6) creating foam formation. The impact of base titrant on Type 19A polysaccharide and protein levels was examined. Two 3 L fermentors were set up with one fermentor serving as the original process control, using 20% $Na_2CO_3$ solution (w/v) as the base feed. The other fermentor used 3 N NaOH as the base feed.

Figure 1:
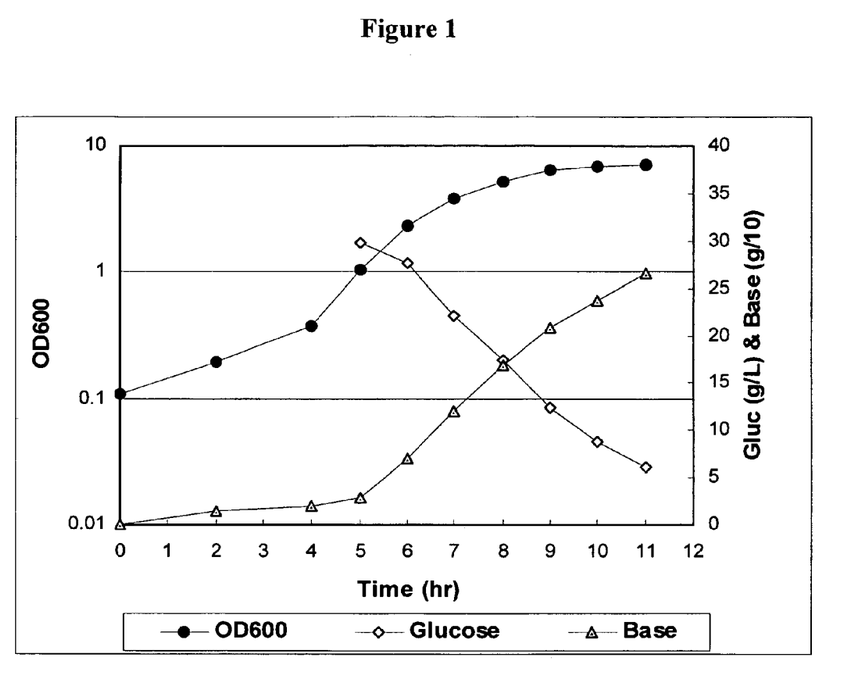
FIG. 1 shows the optical density (OD), base and glucose levels during the fermentation phase with $Na_2CO_3$ as titration base from laboratory studies at 3 L scale. Base in grams is divided by 10 for plotting purposes.
Figure 2:
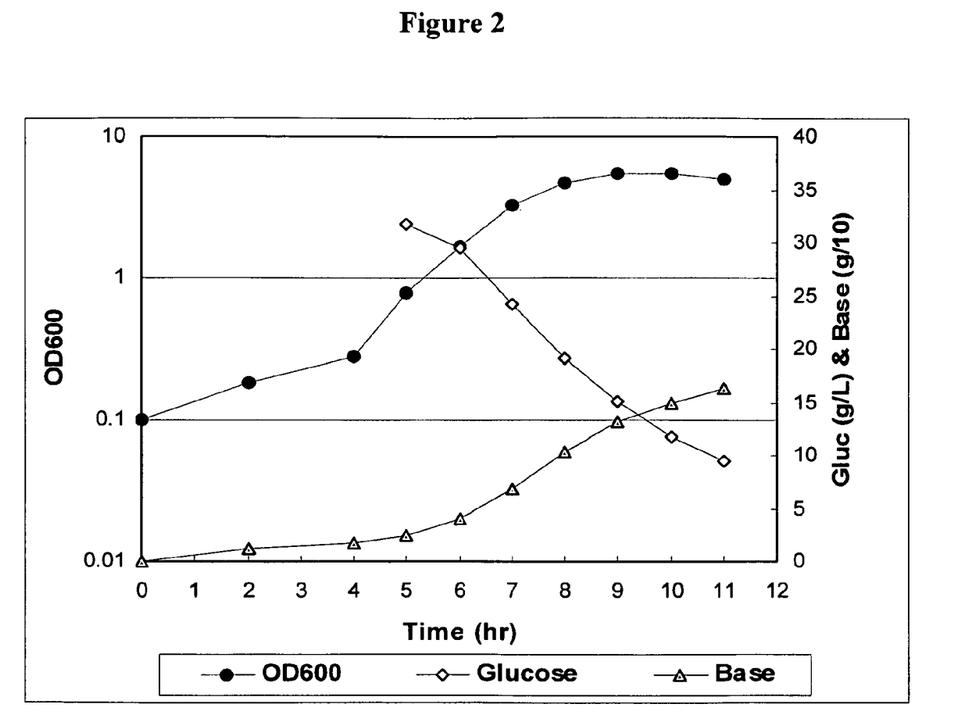
FIG. 2 shows the optical density (OD), base and glucose levels during the fermentation phase with NaOH as titration base from laboratory studies at 3 L scale. Base in grams is divided by 10 for plotting purposes.

During the recovery phase, cells were lysed in the fermentor with DOC (final concentration 0.13% (w/v)) with the fermentor held at 36° C. for 30 minutes. Following this step, the lysate was held overnight with agitation at ambient temperature (22° C.). After the lysate hold, the lysate was pH titrated through a range from unadjusted to 4.5 with samples pulled at various pH setpoints. These samples were held overnight at ambient temperature prior to being processed and analyzed for polysaccharide and protein concentrations. The OD, base and glucose levels during the fermentation phase are shown in FIG. 1 and FIG. 2. The major difference was a higher final OD for the carbonate run.

Figure 3:
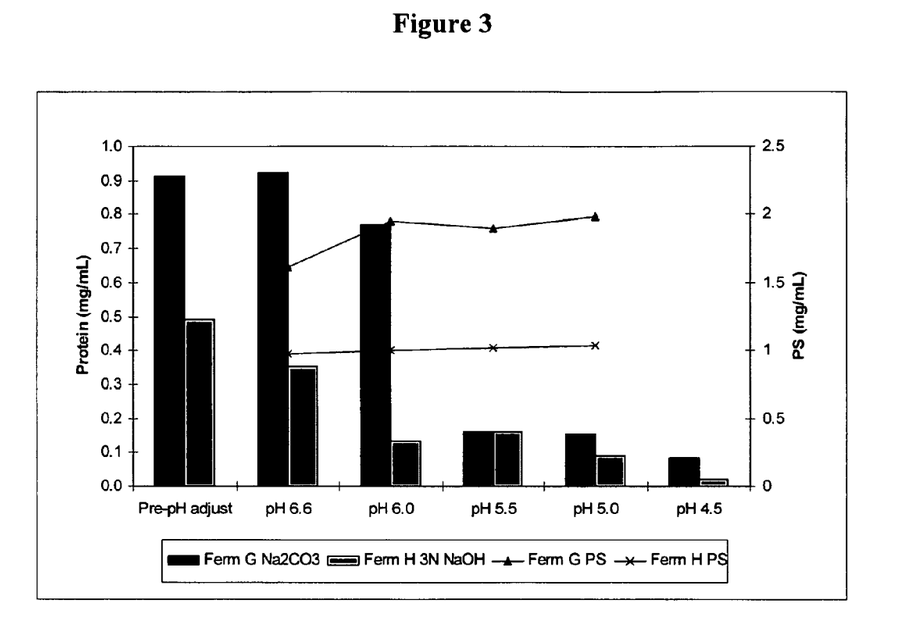
FIG. 3 shows total protein and polysaccharide results at different pH adjustments for alternate base feeds of $Na_2CO_3$ or NaOH.

The effect of post DOC lysate pH adjustment on total protein levels was also examined, and is shown in FIG. 3. The lower pH levels reduced the protein load in cell free broth for both the NaOH run and the $Na_2CO_3$ run. The lower pH (<6.6) had no negative impact on the polysaccharide yield. The fermentation analysis results served as an indication that the NaOH base feed was an acceptable alternative to the process using the $Na_2CO_3$ base feed during fermentation, but produced lower yields than what was obtained with the $Na_2CO_3$ feed.

Effect of Base Titrant on 19A Molecular Weight

A set of fermentations at the 3 L scale were performed to determine if the base titrant, HySoy concentration and pH hold step affected serotype 19A molecular weight. The molecular weight determination was performed using MALLS assay following the modified purification process. Results are shown in Table 1.

TABLE 1

Impact of base titrant on 19A molecular weight (L29331-94)

| Run No. | pH/Temp | HySoy | pH Hold | Base | MALLS (kDa) |
|---|---|---|---|---|---|
| D | 7.0/36° C. | 28 g/L | 5.0 | 3 N NaOH | 340 |
| E | 7.0/36° C. | 20 g/L | 5.0 | 3 N NaOH | 350 |
| F | 7.0/36° C. | 20 g/L | 5.0 | 20% $Na_2CO_3$ | 713 |
| H | 7.0/36° C. | 20 g/L | 6.6 | 20% $Na_2CO_3$ | 713 |

Effect of Bicarbonate and Mixed Base pH Titrant

In the first study (Runs L29331-122 and -139), varying levels of initial sodium bicarbonate and base blends of sodium hydroxide and sodium carbonate were used in conjunction with a pH 5.0 hold step after the DOC hold step. The initial bicarbonate additions ranged from 10-50 mM and the sodium carbonate added to 3N sodium hydroxide for the base titrant ranged from 0.2-1.8 M. One run contained 50 mM initial bicarbonate and used NaOH as a base titrant. The carbonate levels at the end of these fermentations ranged from 14-111 mM. Serotype 19A molecular weights ranged from 520 to 713 kDa. Run parameters and results are shown in Table 2.

TABLE 2

Na$_2$CO$_3$ vs. mixed base as pH titrant

| | Run No. | | NaHCO$_3$ (mM) | Base Na$_2$CO$_3$ | NaOH | MALLS (kDa) | PS Yield (mg/mL) |
|---|---|---|---|---|---|---|---|
| Part I | | E | 0 | 20% | 0 | 759 | 0.836 |
| L29331-122 | | F | 10 | 0.2 M | 3 N | 520 | 0.308 |
| 20 g/L HySoy | | G | 10 | 0.4 M | 3 N | 648 | 0.538 |
| | | H | 10 | 0.9 M | 3 N | 563 | 0.334 |
| Part II | | C | 20 | 0.9 M | 3 N | 662 | 1.027 |
| L29331-139 | | D | 20 | 1.8 M | 3 N | 611 | 0.903 |
| 28 g/L HySoy | | G | 50 | 0.9 M | 3 N | 713 | 0.924 |
| | | H | 50 | 0 M | 3 N | 713 | 1.051 |

A second study (L29331-159 and -185) used initial bicarbonate additions of 15-30 mM and base blends using 0.4-1.0 M Na$_2$CO$_3$. The carbonate levels at the end of fermentation ranged from 24-62 mM. Serotype 19A molecular weights ranged from 502 to 763 kDa. Run parameters and results are shown in Table 3.

TABLE 3

NaHCO$_3$ with mixed base as pH titrant

| Run No. | HySoy/DMS | NaHCO$_3$ (mM) | Na$_2$CO$_3$/NaOH | MALLS (kDa) | PS Yield (mg/mL) |
|---|---|---|---|---|---|
| G2 | 28 g/L/60 mL/L | 15 | 1.0 M/3 N | 657 | 0.853 |
| H2 | 28 g/L/60 mL/L | 15 | 0.4 M/3 N | 605 | 0.755 |
| C | 20 g/L/60 mL/L | 20 | 0.4 M/3 N | 571 | 0.386 |
| E | 20 g/L/60 mL/L | 20 | 1.0 M/3 N | 763 | 0.439 |
| F | 20 g/L/60 mL/L | 25 | 0.7 M/3 N | 462 | 0.382 |
| G | 20 g/L/60 mL/L | 30 | 0.4 M/3 N | 502 | 0.355 |
| H | 20 g/L/60 mL/L | 30 | 1.0 M/3 N | 594 | 0.415 |

Comparison of Mixed and Pure Carbonate Titration Base Fermentation Processes

An experiment was performed to compare the base blend process (0.7 M Na$_2$CO$_3$/3 N NaOH) to the carbonate titrant process (20% Na$_2$CO$_3$ solution, w/v). Results (Table 4) confirmed that the molecular weight from the carbonate titrant process was higher and more consistent (778, 781 kDa) than the molecular weight from the base blend process (561-671 kDa). Polysaccharide yield was also higher with the Na$_2$CO$_3$ process.

TABLE 4

Run L29399-1 Na$_2$CO$_3$ vs. mixed base

| Run No. | NaHCO$_3$ (mM) | Base Na$_2$CO$_3$ | NaOH | MW (kDa) | PS Yield (mg/mL) |
|---|---|---|---|---|---|
| C | 25 | 0.7 M | 3 N | 565 | 1.106 |
| D | 25 | 0.7 M | 3 N | 561 | 0.908 |
| E | 25 | 0.7 M | 3 N | 612 | 0.894 |
| G | 25 | 0.7 M | 3 N | 671 | 0.873 |
| F | 0 | 20% | 0 | 778 | 1.282 |
| H | 0 | 20% | 0 | 781 | 1.249 |

Pilot Scale Runs

Several serotype 19A pilot scale (100 L) runs with various base titrants were performed. The molecular weight determination was performed using MALLS assay following a complete purification process and is reported from the final purified batch. Results are shown in Table 5.

TABLE 5

Impact of base titrant on 19A molecular weight at pilot scale

| Fermentation Batch | Titration Base | Purification Batch | FBC MALLS (kDa) |
|---|---|---|---|
| RRP19A-0008 | 3 N NaOH | L26563-10 | 390 |
| RRP19A-0009 | 3 N NaOH | L26563-11 | 380 |
| IPPPN19A-005 | 3 N NaOH/0.6 M Na$_2$CO$_3$ | L26260-37 | 492 |
| IPPPN19A-006 | 3 N NaOH/0.6 M Na$_2$CO$_3$ | L26260-38 | 480 |
| IPPPN19A-007 | 3 N NaOH/0.6 M Na$_2$CO$_3$ | L26260-39 | 490 |
| IPPPN19A-014 | 20% Na$_2$CO$_3$ | L26260-49 | 580 |
| IPPPN19A-016 | 20% Na$_2$CO$_3$ | L26260-50 | 559 |
| IPPPN19A-017 | 20% Na$_2$CO$_3$ | L26260-51 | 599 |

Effect of Base Titrant and Overlay on 19A Molecular Weight

A set of fermentations at the 3 L scale were performed to determine if the base titrant and atmospheric overlay affected the molecular weight. The molecular weight determination was performed using MALLS assay following the modified purification process. Results are shown in Table 6.

TABLE 6

Impact of base titrant and overlay on 19A molecular weight

| Run No. | Base | Overlay | MALLS (kDa) |
|---|---|---|---|
| Control | 3 N NaOH | Air | 350 |
| C | 0.7 M Na$_2$CO$_3$ | Air | 855 |
| D | 1.5 M Na$_2$CO$_3$/1.5 N NaOH | Air | 710 |
| E | 3 N NaOH | 100% CO$_2$ | 634 |
| F | 3 N NaOH | 50% CO$_2$ | 646 |
| G | 3 N NaOH | 20% CO$_2$ | 567 |
| H | 3 N NaOH | 10% CO$_2$ | 547 |

Effect of Harvest Time on 19A Molecular Weight

The impact of harvest time on the molecular weight of serotype 19A polysaccharides was also studied. Table 7 summarizes data from one run showing a decrease in MW as a function of the fermentation OD and harvest time.

TABLE 1

MW as a Function of Fermentation OD and Harvest Time

| OD (Time) | MALLS |
|---|---|
| 2.2 (3 hrs) | 1065 |
| 4.2 (4 hrs) | 845 |
| 5.5 (5.5 hrs) | 756 |
| 5.9 (6.6 hrs) | 653 |

Figure 4:
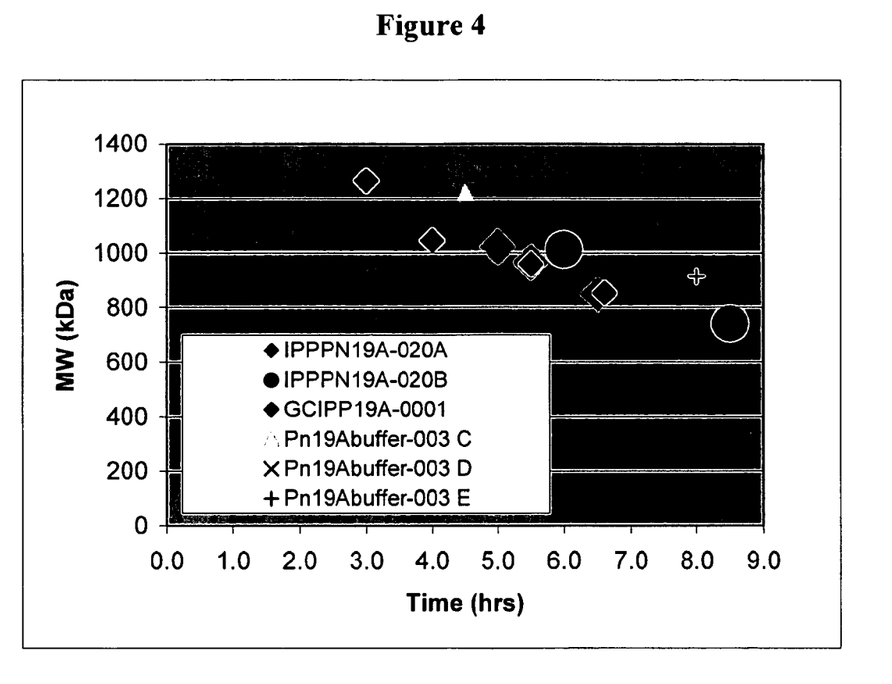
FIG. 4 shows molecular weight as a function of fermentation harvest time in the production of 19A polysaccharides.
Figure 5:
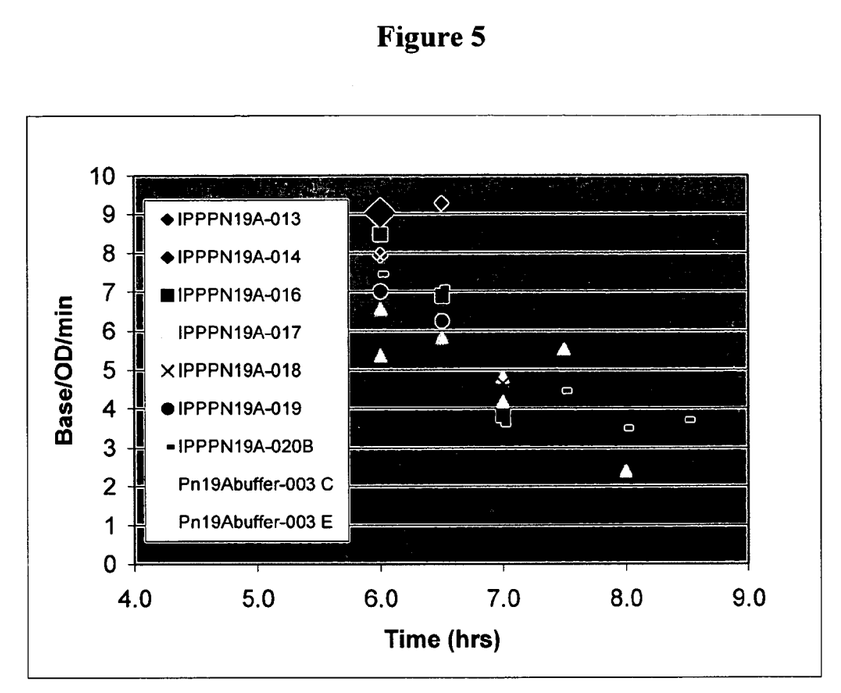
FIG. 5 shows specific base consumption per time per optical density (OD) as a function of harvest time in the production of 19A polysaccharides. Base in grams is divided by 10 for plotting purposes.
Figure 6:
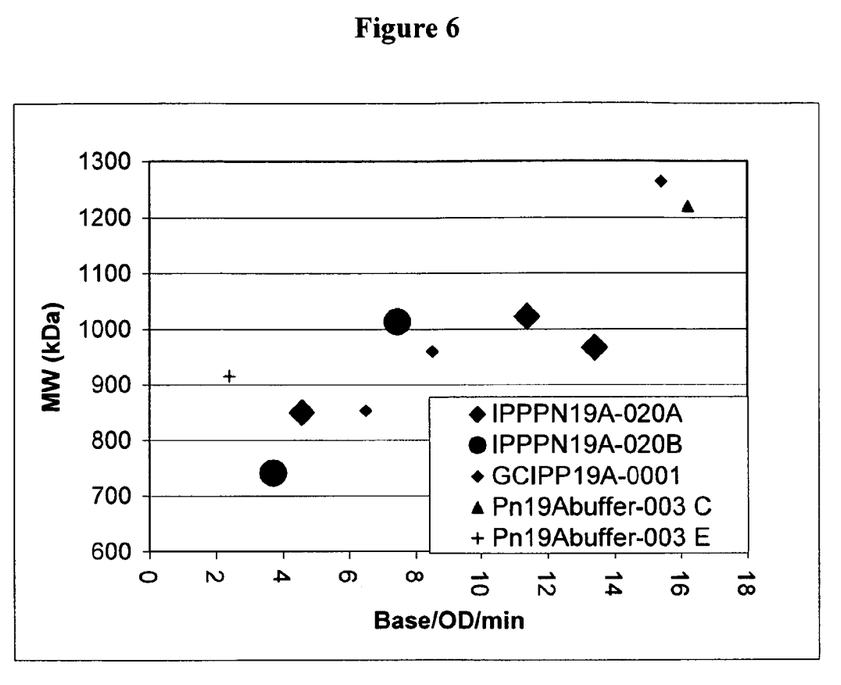
FIG. 6 shows molecular weight as a function of specific base utilization in the production of 19A polysaccharides.

Further studies with several experimental runs also showed a decrease in MW as a function of fermentation OD and harvest time. FIG. 4 shows molecular weight as a function of fermentation optical density (OD) and harvest time in the production of 19A polysaccharides. FIG. 5 shows specific base consumption per time per optical density (OD) as a function of harvest time in the production of 19A polysaccharides. FIG. 6 shows molecular weight as a function of specific base utilization in the production of 19A polysaccharides.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

That which is claimed:

1. A method for producing a solution containing high molecular weight isolated *Streptococcus pneumoniae* serotype 19A capsular polysaccharides, the method comprising:
    a) preparing a fermentation culture of *Streptococcus pneumoniae* bacterial cells that produce serotype 19A capsular polysaccharides;
    b) fermenting said fermentation culture for less than 6 hours;
    c) lysing the bacterial cells in said fermentation culture; and
    d) isolating *Streptococcus pneumoniae* serotype 19A capsular polysaccharides from said fermentation culture;
whereby a solution containing high molecular weight isolated *Streptococcus pneumoniae* serotype 19A capsular polysaccharides is produced.

2. The method of claim 1, wherein said high molecular weight isolated *Streptococcus pneumoniae* serotype 19A capsular polysaccharide has a molecular weight of at least 480 kD.

3. The method of claim 1, wherein step c) comprises fermenting said fermentation culture for less than 5 hours.

4. The method of claim 1, wherein step c) comprises fermenting said fermentation culture for less than 4 hours.

5. The method of claim 1, wherein step c) comprises fermenting said fermentation culture for between 3 hours and 6 hours.

6. A method for producing a solution containing high molecular weight isolated *Streptococcus pneumoniae* serotype 19A capsular polysaccharides, the method comprising:
    a) preparing a fermentation culture of *Streptococcus pneumoniae* bacterial cells that produce serotype 19A capsular polysaccharides;
    b) supplying $CO_2$ to said fermentation culture;
    c) fermenting said fermentation culture for less than 6 hours;
    d) lysing the bacterial cells in said fermentation culture; and
    e) isolating *Streptococcus pneumoniae* serotype 19A capsular polysaccharides from said fermentation culture;
whereby a solution containing high molecular weight isolated *Streptococcus pneumoniae* serotype 19A capsular polysaccharides is produced.

7. The method of claim 6, wherein said high molecular weight isolated *Streptococcus pneumoniae* serotype 19A capsular polysaccharide has a molecular weight of at least 480 kD.

8. The method of claim 6, wherein step c) comprises fermenting said fermentation culture for less than 5 hours.

9. The method of claim 6, wherein step c) comprises fermenting said fermentation culture for less than 4 hours.

10. The method of claim 6, wherein step c) comprises fermenting said fermentation culture for between 3 hours and 6 hours.

11. The method of claim 6, wherein supplying $CO_2$ to said fermentation culture comprises adding bicarbonate ion ($HCO_3^-$) to the fermentation culture.

12. The method of claim 11, wherein adding $HCO_3^-$ to the fermentation culture comprises adding $NaHCO_3$.

13. The method of claim 6, wherein supplying $CO_2$ to said fermentation culture comprises adding carbonate ion ($CO_3^{2-}$) to the fermentation culture.

14. The method of claim 13, wherein adding $CO_3^{2-}$ to the fermentation culture comprises adding $Na_2CO_3$.

15. The method of claim 6, wherein supplying $CO_2$ to said fermentation culture comprises a first addition of $NaHCO_3$ and a second addition of $Na_2CO_3$.

16. The method of claim 6, wherein supplying $CO_2$ to said fermentation culture comprises overlaying the fermentation culture with $CO_2$.

* * * * *